US005144949A

United States Patent [19]

Olson

[11] Patent Number: 5,144,949
[45] Date of Patent: Sep. 8, 1992

[54] DUAL CHAMBER RATE RESPONSIVE PACEMAKER WITH AUTOMATIC MODE SWITCHING

[75] Inventor: Walter H. Olson, North Oaks, Minn.

[73] Assignee: Medtronic, Inc., Minneapolis, Minn.

[21] Appl. No.: 669,790

[22] Filed: Mar. 15, 1991

[51] Int. Cl.[5] ............................................. A61N 1/368
[52] U.S. Cl. ............................................. 128/419 PG
[58] Field of Search ................................... 128/419 PG

[56] References Cited

U.S. PATENT DOCUMENTS

| | | | |
|---|---|---|---|
| 4,527,568 | 7/1985 | Rickards | 128/419 PG |
| 4,856,523 | 8/1989 | Sholder et al. | 128/419 PG |
| 4,932,406 | 6/1990 | Berkovits | 128/419 PG |
| 5,085,215 | 2/1992 | Nappholz et al. | 128/419 PG |

Primary Examiner—William E. Kamm
Assistant Examiner—Kennedy J. Schaetzle
Attorney, Agent, or Firm—Harold R. Patton; John A. Rissman; Greg P. Gadson

[57] ABSTRACT

A dual chamber rate responsive pacemaker with automatic mode switching between the DDD mode, the VVIR mode, and the DDIR mode, based on the difference between the average sensor rate and the average atrial rate. The primary pacing mode of operation is DDD, unless that mode is contraindicated by too great a difference between the average sensor rate and the average atrial rate. When the average sensor rate and average atrial rates are not too different, the DDD mode prevails. During bouts of sustained atrial tachyarrhythmia or atrial oversensing, the average atrial rate is greater than the average sensor rate. When that difference exceeds a programmable function of the two rates, the mode is switched to VVIR to avoid tracking high atrial rates. Conversely, if there is atrial chronotropic incompetence or atrial undersensing, then the average sensor rate is greater than the average atrial rate. If that difference exceeds a second programmable function of the two rates, then the system switches mode to DDIR to provide increased rate response and to preserve AV synchrony. Fallback, riseup, hysteresis at switching boundaries, average atrial rate computation, atrial upper rate limit (AURL), sensor upper rate limit (SURL), use of refractory atrial sensed events for P-P intervals, synchronization when switching to DDD mode, blanking and refractory periods are set forth herein.

22 Claims, 6 Drawing Sheets

DUAL CHAMBER RATE RESPONSIVE PACEMAKER WITH AUTOMATIC MODE SWITCHING

BACKGROUND OF THE INVENTION

1. Field of the Invention

This invention relates to cardiac pacemakers, and more particularly to pacemakers which combine sensor based, rate determining algorithms with atrial synchronized pacing in dual chamber rate responsive modes of physiologic pacing.

2. Description of the Prior Art

The commonly assigned U.S. Pat. No. 4,932,406 (incorporated herein by reference) sets forth the prior art of single and dual chamber pacing and physiologic sensor based rate responsive pacing. Dual chamber DDD physiologic pacemakers following the teachings of U.S. Pat. No. 4,312,355 to Funke may be characterized as possessing a number of different pacing modes which are switched in or out in the presence or absence of atrial and ventricular events. Such DDD pacemakers are constantly updating their functional modes at the end of programmed escape intervals or upon earlier occurring atrial and ventricular events. However, DDD pacemakers do not switch modes in the sense that that expression has been defined in the art.

"Mode switching" connotes a semi-permanent mode change driven by sensed heart activity events and/or sensor derived events occurring in a first relationship wherein the device dictates that it remain in the mode it is changed to until those or other events satisfy a second defined relationship. Individual "modes" define sets of rules for the operating states of the machine. In the pacing context, the rules define the pacing and sensing operating conditions from instant to instant irrespective of higher level monitoring of cardiac and physiologic signals which are used to initiate switching between modes, depending on a further set of mode switching rules. These "modes" include the major or principal operating modes and transition modes as described hereinafter.

For example, one of the earliest mode switching devices is illustrated by pacemakers exhibiting hysteresis and particularly pacemakers of the type described in U.S. Pat. Nos. 4,363,325 to Roline et al and U.S. Pat. No. 3,999,557 to Citron. In the '325 patent, a pacemaker capable of operating in the atrial synchronous ventricular inhibited (VDD) mode automatically switches to the VVI mode at a preset atrial sense driven upper rate. The mode is switched back to VDD at a detected lower atrial sense driven lower rate. In the '557 patent, a VVI pacemaker remains "off" until a bout of extreme bradycardia (a heart rate less than 30 bpm) is detected, whereupon the VVI pacemaker switches "on" (at a lower rate of 70 bpm, for example). Thereafter the pacemaker remains in the VVI mode.

Contemporaneously with the introduction of dual chamber pacing, particularly DDD pacing, single chamber and subsequently dual chamber rate responsive pacemakers were developed as described in the aforementioned application. With the introduction and incorporation of physiologic sensors into single and dual chamber pacemakers, a four letter code denoting the principal modes of operation of pacemakers with and without physiologic sensors and rate adaptive pacing capabilities was published in "The NASPE/BPEG Pacemaker Code" by the A. Berstein al, PACE 10(4), Jul-Aug, 1987, which updated the three letter code published in the American Journal of Cardiology 34:487 (1974). The incorporation of physiologic sensors added impetus to the acceptance of the "mode switching" vernacular. Merely by adding a physiologic sensor, the pacemaker, regardless of whether it possessed only single chamber or dual chamber pacing capabilities, became susceptible to at least two modes of operation, that is, a first mode dictated by the heart rate, and a second mode dictated by the sensor derived rate. Thus, pacemakers with sensors for detecting physiologically required pacing rates (other than the underlying atrial and/or ventricular natural depolarization rates) switched modes between the sensor derived rate and the natural cardiac depolarization derived rate as taught, for example, in U.S. Pat. No. 4,890,617, incorporated herein by reference.

Consequently, the current vernacular for "mode switching" in the rate responsive pacing context suggests that the pacing mode of operation at any given time may be switched from a mode driven exclusively by the intrinsic heart rate during one period of time and the physiologic sensor derived heart rate during another period of time. In that context, the aforementioned '406 patent suggests a form of mode switching from the recognized DDD mode to the VVIR mode and back to the DDD mode under certain conditions related to the relationship between the natural atrial rate and a fallback limit rate. The solution to the problem of tracking the atrial rate in relation to a sensor derived rate proposed by the '406 patent encompasses switching modes between the DDD mode and the VVIR mode with specified transition mode and pacing rate rise-up and fallback behaviors.

Pacing in the VVIR mode may unnecessarily constrain the contribution of the atrial chamber of the heart in those situations when the physiologic sensor derived rate compared to the average atrial rate indicates that the atrium is chronatropically incompetent or that atrial undersensing is being experienced. It is generally desirable to maintain atrial contribution whenever possible and to maintain a certain smoothness in the stimulation rate between upper and lower rate limits.

It is also generally desirable to use the simplest modes possible to control the beat by beat operation of the system dependant upon two separate rate modifiers, that is, the instantaneous atrial rate in atrial synchronous modes and the average (combined) sensor driven rate in rate responsive modes. Moreover, it is desirable to maintain DDD pacing, that is, to track the atrial rate, whenever reasonable, and to switch modes only when accumulated evidence is available that the atrial rate is pathologic, noise, or incorrectly sensed. Reliance on the sensor driven rate should be minimized and limited only to situations where pathologic atrial tachycardia or atrial bradycardia are indicated given the inherent inferiority in specificity and reliability of man-made implanted sensors.

In addition, it is desirable that a smooth rate transition or a rate transition that is not felt by the patient be achieved. On the other hand, the system should not oscillate indecisively between modes or be too sensitive. In addition, pacing hemodynamics should not be compromised between or during transitions.

SUMMARY OF THE INVENTION

In accordance with the present invention, a mode switching pacemaker employs one or more physiologic sensors to develop an average combined sensor rate independently of the average atrial rate. A sensor upper rate limit and an atrial upper rate limit are needed to constrain the pacing rate within the bounds of the pacer's lower rate and the atrial upper rate to maintain DDD pacing wherever possible and to use the sensor rate only when a pathologic atrial tachycardia or bradycardia manifests itself In accordance with the present invention, the pacemaker avoids employing the DDDR mode and switches between DDD and DDIR modes, or between DDD and VVIR modes, based on the difference between the average combined sensor rate and the average atrial rate at a given time. The DDD mode is the primary mode of operation unless it is contraindicated by too great a difference between the average sensor rate and the average atrial rate. In accordance with the present invention, whenever the sensor rate and the atrial rate are not too different, there is approximate agreement on the rate, so the mode should be maintained in DDD mode up to the atrial upper rate limit in order to maintain AV synchrony.

During bouts of sustained atrial tachyarrhythmias, noise, or atrial oversensing, the average atrial rate exceeds the averaged combined sensor rate. If the atrial rate exceeds the sensor rate by a programmable function of the two rates (the A-S function), the system of the present invention switches from DDD to VVIR mode to avoid tracking the high atrial rate. Conversely, if the average combined sensor rate exceeds the atrial rate by a second programmable function of the two rates (the S-A function), then the system of the present invention switches from the DDD mode to the DDIR mode to preserve AV synchrony at the sensor rate without atrial competition.

In accordance with the present invention, at the point in the tracking of the average atrial rate (AAR) and the average combined sensor rates (ACSR) that the difference exceeds bounds set by the A S function, the VVIR mode is invoked immediately, and ventricular pacing commences at the current average atrial rate, but falls back to the rate indicated by the sensor(s) to allow the ventricular pacing rate to track the ACSR. This VVIR fallback mode alleviates sudden rate changes while conforming the pacing rate to the sensor indicated rate.

Conversely, at the point in time when the AAR (which is monitored during the VVIR mode operation) falls back toward the ACSR, the difference between the AAR and the ACSR falls below bounds set by the A-S function, the VVIR pacing rate is caused to increase in a riseup mode until it matches or exceeds the instantaneous atrial rate and synchronizes to the then prevailing atrial rate. Thereafter, the system of the present invention switches to the DDD mode, and ventricular pacing follows the detected atrial rate, as necessary.

Advantageously, the aforementioned mode switching operations may take place within the range between the pacing lower rate limit (LRL) and the sensor derived upper rate limit (SURL) and sustained pacing at either the SURL or the atrial upper rate limit (AURL) may be avoided. However, in certain circumstances, that is, when the ACSR exceeds the SURL the mode switches to the DDIR mode at the sensor upper rate limit. When in the DDIR mode, the intrinsic atrial rate is absent due to sensor driven atrial pacing.

The riseup occurs either at the point where the difference between the ACSR and the AAR exceeds the programmable S-A function, or when the ACSR exceeds the SURL, whichever occurs first. The DDIR mode of operation continues even if the ACSR falls back below the SURL but only until the underlying instantaneous atrial rate again exceeds the ACSR, whereupon the system of the present invention switches back to the DDD mode using the synchronization process and ventricular pacing tracks the instantaneous atrial rate up to the AURL or until the AAR again exceeds the ACSR by the programmable A-S function.

The system of the present invention thus avoids operating at the AURL and instead relies on the ACSR in order to avoid tracking sustained atrial tachyarrhythmias even if below the AURL. Conversely, in the presence of atrial bradycardia, the system of the present invention provides atrial sequential pacing, at least up to the SURL. Fallback and rise-up transition modes between principal operating modes are provided to smooth the transition while avoiding indecisive oscillations between the principal or major operating modes.

These and other advantages and features of the present invention will be apparent from the following description of the accompanying drawings which illustrate preferred embodiments exemplifying the best modes of carrying out the invention as presently perceived.

BRIEF DESCRIPTION OF THE DRAWINGS

Reference is now made to the accompanying detailed drawings of the preferred embodiments, in which like referenced numerals represent like or similar parts throughout, in which.

DESCRIPTION OF THE PREFERRED EMBODIMENT

Figure 1:
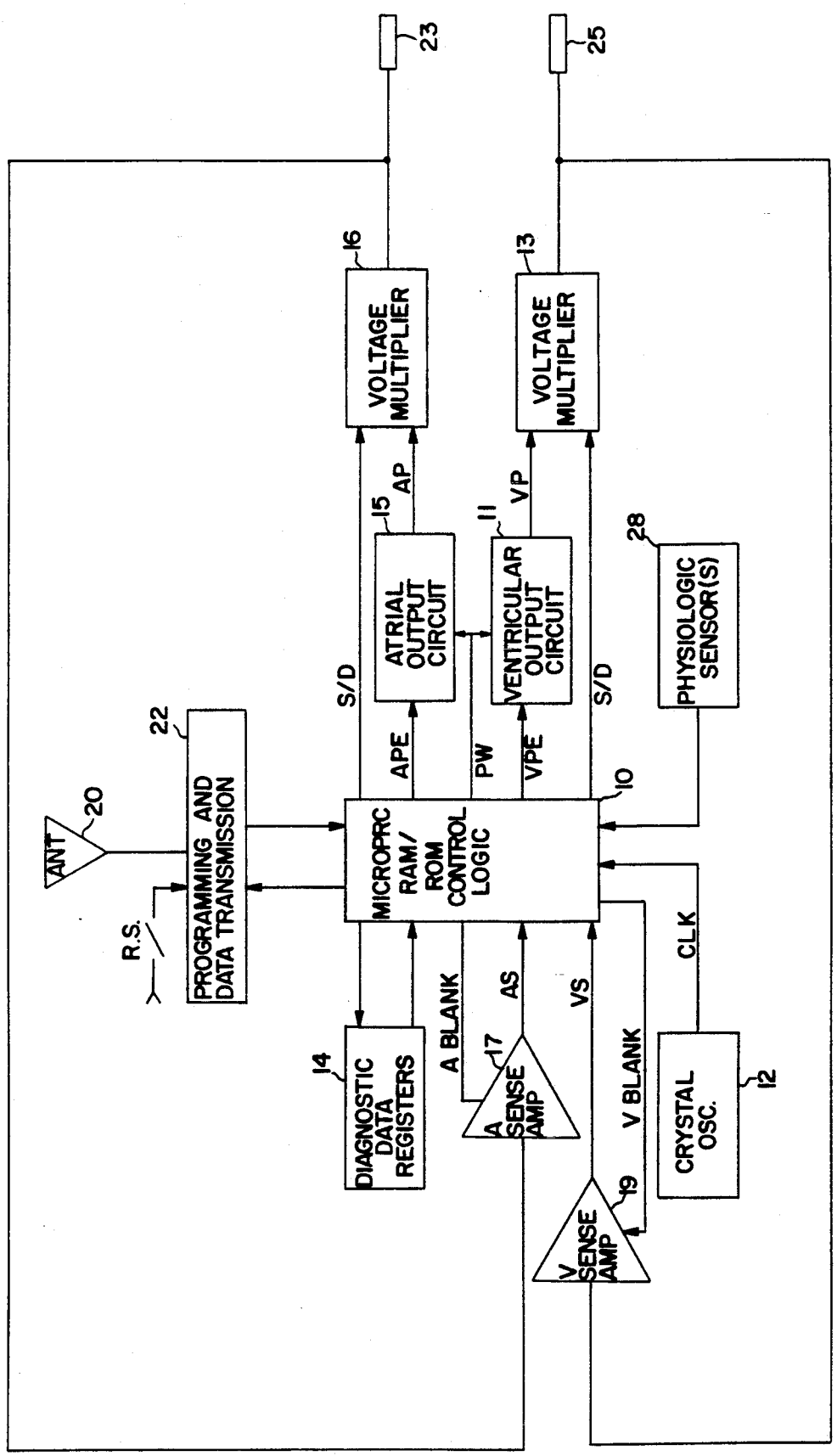
FIG. 1 is a simplified block diagram of the mode switching hardware pacing system of the present invention.

Hardware suitable for practicing the present invention includes the Medtronic Dysrhythmia Research Instrument which is available from Medtronic, Inc., Fridley, Minnesota. This machine is a computer based physiologic stimulator operating under the control of software. The computer hardware is interfaced with the heart through atrial and ventricular sense amplifiers and an atrial and ventricular pulse generators. U.S. Pat. No.

4,577,633, which is incorporated by reference, describes this computer driven stimulator in more detail.

An additional interface must be added to permit the integration of a sensor for the estimation of activity and metabolic demand by the patient A suitable sensor is disclosed in U.S. Pat. No. 4,428,378 to Anderson and Brumwell, which sets forth the structure for monitoring physical activity of the body to set a pacing rate. This patent is also incorporated by reference. Other possible sensors are described in "A Review of Pacemakers That Physiologically Increase Rate: The DDD and Rate-Responsive Pacemakers", by Fearnot et al., published in *Progress in Cardiovascular Diseases*, Vol. XXIX, No. 2, 1986, pp. 145-164. It is anticipated that the present invention may advantageously employ two or more such sensors to develop an ACSR control signal.

In the preferred embodiment of the present invention, the three principal pacing modes are defined as follows:

VVIR—in VVIR mode, the pacemaker not only delivers stimuli to the ventricular lead, but also senses the electrogram from the same lead. Sensing of the spontaneous ventricular activity (VS) will reset pacemaker timing and inhibit the (VP) stimulus. As a result, the pacemaker will remain inhibited as long as the spontaneous ventricular rate is higher (interval between VS events is shorter) than the activity sensor modulated lower pacing rate. The higher the activity level, the shorter the "lower rate" pacing escape interval will be. Ventricular sensing or pacing starts a programmable ventricular refractory period. During the first part of that period called "ventricular blanking period", the sensing system is completely blind. The remainder of the refractory period is the so called "noise sampling period". Ventricular sensed events in that period will not reset the timing of the generator but will start a new refractory period including blanking and noise sampling. Repeated sensing caused by noise on the lead results in pacing at the sensor modulated pacing rate. During the VVIR mode in the present invention, the atrium is sensed to determine the AAR which may be used to switch to another mode.

DDD—the essence of DDD pacing is the maintenance of the AV synchrony and atrial rate response under all circumstances. As long as the spontaneous atrial sensed rate remains between the programmed upper and lower pacing rates, the pacemaker synchronizes ventricular stimuli to atrial P-waves. An atrial interval longer than the programmed lower interval initiates AV sequential, DVI pacing. An atrial interval shorter than the programmed minimum interval induces either pseudo-Wenckebach behavior or 2:1 block in the synchronization in the pacemaker. Sensing of a spontaneous ventricular complex inhibits both the ventricular and atrial stimulation and resets the timing. Atrial stimulation and sensing start an AV interval and an atrial refractory period. Ventricular stimulation or sensing starts a ventricular minimum pacing rate (lower rate) and both atrial and ventricular refractory periods. Atrial stimulation will initiate a programmable "cross-blanking" of ventricular sensing, and, if this is programmed on, a ventricular safety pacing interval.

DDIR—in this mode, the capability for pacing and sensing is present in both chambers; however, sensed atrial activity will inhibit the atrial output pulse but will not affect the timing of the ventricular output. DDI mode has advantages over DVI pacing mode because it avoids atrial competitive pacing through sensing the atrial signal. AV sequential (DVI) pacing will be provided by default in the absence of intrinsic atrial activity. Additionally, intrinsic ventricular activity occurring during the AV delay will inhibit ventricular pacing and reset timing. Atrial sensed actions during the non-atrial refractory period will inhibit the AP output only. This sensing will not affect timing of the VA and AV intervals, and in the absence of ventricular activity, a ventricular output pulse will be provided at the end of the sensor derived VV interval or at the end of the programmed lower or upper pacing In addition, the following acronyms are used in the specification:

AAR: Average Atrial Rate derived from AS and AR events

ABLANK: Atrial sense amplifier blanking signal

ACSR: Average Combined Sensor Rate derived from output of one or more sensors whose sensitivity and weighting factor may be programmed AP: Atrial Pace event APE: Atrial Pace Enable signal AR: Atrial sensed event during an atrial refractory period AS: Atrial Sensed event AURL: A programmable AS driven atrial upper pacing rate limit expressed in beats per minute AV: Ventricular escape interval from AP or AS to scheduled VP.

DDIr: DDIR mode as defined above, but with pacing rate varying as a riseup transition function when switching from DDD to the DDIR mode f(A-S)n: A programmable set of threshold value functions of the difference between AAR and ACSR when AAR is greater than ACSR over a range of pacing rates between the LRL and the AURL and the SURL f(S-A)$_n$: A programmable set of threshold value functions of the difference between the ACSR and AAR when ACSR is greater than AAR over a range of pacing rates between the LRL and the AURL and SURL INT: Sensor defined or average atrial interval (i.e., the interval in ms is 60,000/rate in bpm)

LRL: A programmable lower AP and/or VP rate limit

PMT: Pacemaker Mediated Tachycardia

PVARP: Post Ventricular Atrial Refractory Period

PVARPEXT: PVARP extension, a programmable value to cover the retrograde conduction period for a patient PVC: Premature Ventricular Contraction PW: Pulse Width control signal S/D: Single/Double output pulse amplitude control signal SURL: A programmable sensor driven upper pacing rate limit expressed in beats per minute TARP: Total Atrial Refractory Period=AV interval+PVARP VA: Atrial escape interval from VP or VS to scheduled AP (or retrograde conduction time from ventricular event to retrograde AS)

VBLANK: Ventricular sense amplifier blanking signal

VP: Ventricular Pace event

VPE: Ventricular Pace Enable signal

VRP: Ventricular Refractory Period

VS: Ventricular Sense event

VV: The ventricular escape interval in VVIR or VVIr pacing modes

VVIr: VVIR mode as defined above but with pacing rate varying as a riseup or fallback transition function between the AAR and the ASCR while monitoring the ACSR In the context of the present invention, the DDD, DDIR and VVIR modes are embodied in the system depicted in FIG. 1 in conjunction with the state diagram of FIG. 5. The system depicted in FIG. 1 illustrates the major components of a DDDR pacemaker such as a Medtronic Model 7074 Elite ™ pacemaker and includes a digital logic and/or microprocessor based control logic block 10 (including on board RAM and ROM memory and a central processing unit, in the microprocessor based system). Those major components further include the crystal oscillator 12, diagnostic data registers 14, one or more physiologic sensors 21, antenna 20 and programming and data transmission block 22, and the atrial and ventricular input and output sections coupled to the atrial and ventricular electrodes 23 and 25 adapted to be positioned in the atrium and ventricle of the heart. The atrial pacing output stages include the atrial output circuit 15 and pulse generator 16 coupled to the electrode 23 and the control logic block 10. Similarly, the ventricular output stages include the ventricular output circuit 11 and ventricular pulse generator 13 coupled to the ventricular electrode 25 and the control logic 10. The atrial and ventricular output circuits 15 and 11 receive APE and VPE signals and the programmed PW signal from control logic 10 and respond by providing AP and VP trigger signals to voltage multipliers 16 and 13 respectively. Very simply, when the control logic 10 times out the VA and AV intervals, respective atrial and ventricular pacing impulses having pulse widths determined by the PW signal and amplitudes determined by the S/D signal are supplied to the electrodes 23 and 25.

At that same time, the atrial and ventricular sense amplifiers 17 and 19, respectively, are blanked by ABLANK and VBLANK signals from the control logic 10, and respective atrial and ventricular refractory periods (TARP, PVARP, VRP) are commenced. The atrial and ventricular sense amplifiers 17 and 19, when unblanked, sense the respective atrial and ventricular depolarizations of the heart (P waves and R-waves respectively) and develop the AS and VS signals respectively.

It is the function of the control logic 10 to respond to the AS, VS and sensor input signals to develop the above listed AAR, ACSR, PVARPEXT, TARP, AP and VP signals and the AV and VA intervals all under the control of the programmed mode and parameter value selections stored in memory including the programmed LRL, SURL, AURL, f(A-S)$_n$, f(S-A)$_n$ functions, AV, VA, VRP, and PVARP values.

In practice, digital logic and microprocessor based pacing systems employ a high frequency crystal oscillator 12 to develop clock signals to increment or decrement counters to time out the above-listed intervals. It is common practice to describe the functions of and to program pacemakers in terms of "intervals" (AV, PVARP, blanking, AIW, etc.) or in terms of "rates" (LRL, SURL, AURL, etc.), and it should be understood that the parameters expressed in rates will be implemented in practice as intervals. Because of the use of fixed frequency clocks (except for the use of voltage controlled oscillators in certain instances where the state of the system power source is important), linear depictions of rate behavior will be somewhat non linear over ranges of interest in actual implementation.

As stated hereinbefore, in the context of the present invention, if the average AAR does not exhibit atrial tachyarrhythmia or bradyarrhythmia, DDD pacing is the preferred mode of pacing. The pacemaker of the present invention is designed to stay in the DDD mode as long as the AAR and the ACSR are within a user selected range, that is, within the range defined by the programmable A-S and S-A functions, and the AAR is not in excess of the AURL or is not irregular at higher rates. During episodes of sinus bradycardia and chronotropic atrial incompetence, the atrial rate is not adequate, so the preferred mode of pacing becomes the DDIR mode. Conversely, when significant atrial tachyarryhthmias are detected, the preferred mode is the VVIR mode to avoid inappropriate atrial tracking, atrial competitive pacing and the risk of inducing more atrial arrhythmias. The mode switching between the selected modes depends on a comparison between the AAR and the ACSR up to the AURL and the SURL. In accordance with the present invention, rise up and fall back tracking of the atrial and sensor rates is defined to take place over several heart beats or over a predetermined period of time measured in milliseconds.

Figure 2:
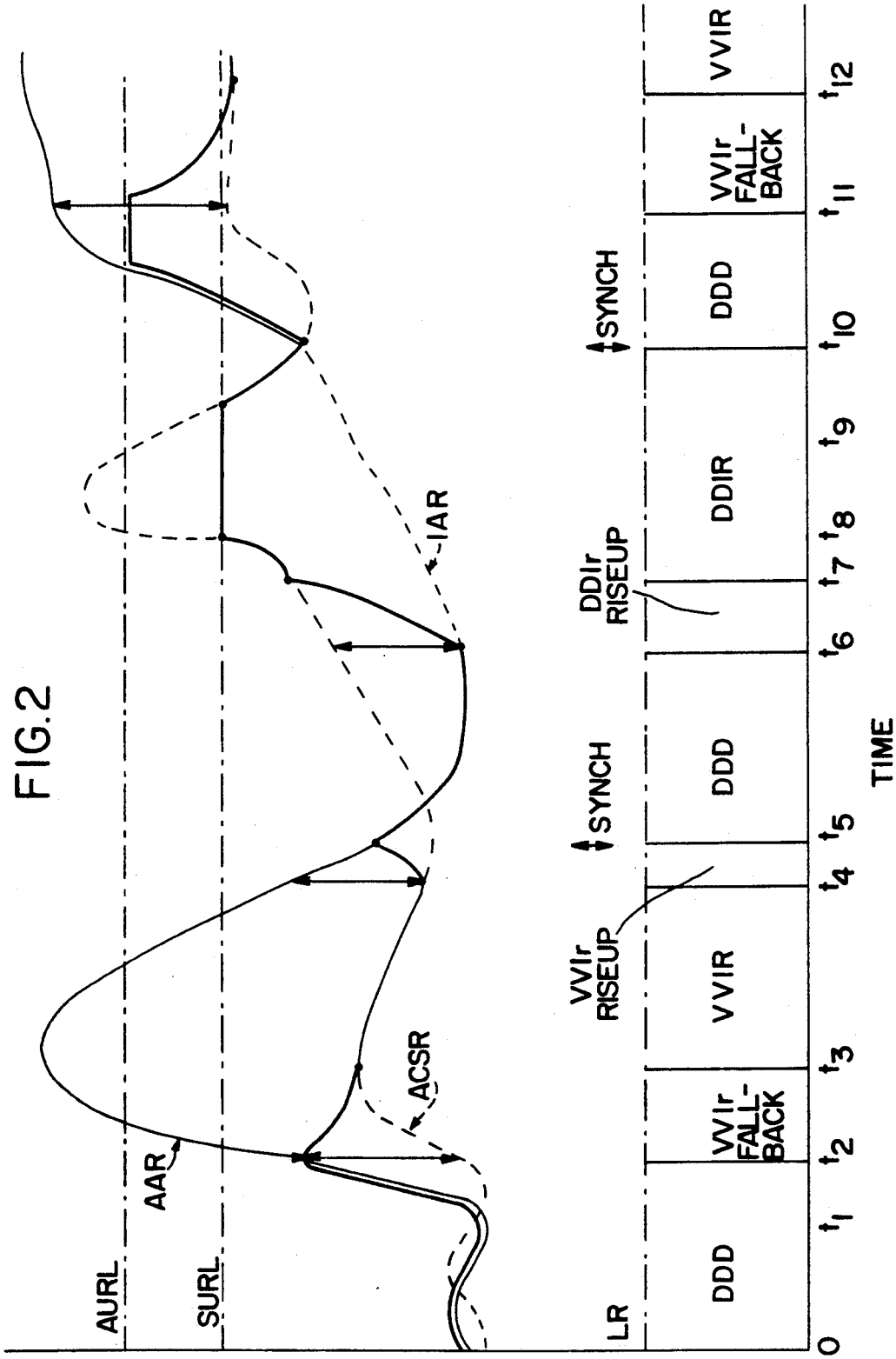
FIG. 2 is an exemplary illustration of the automatic mode switching of the system of the present invention in tracking the AAR and the ACSR over time.
Figure 3:
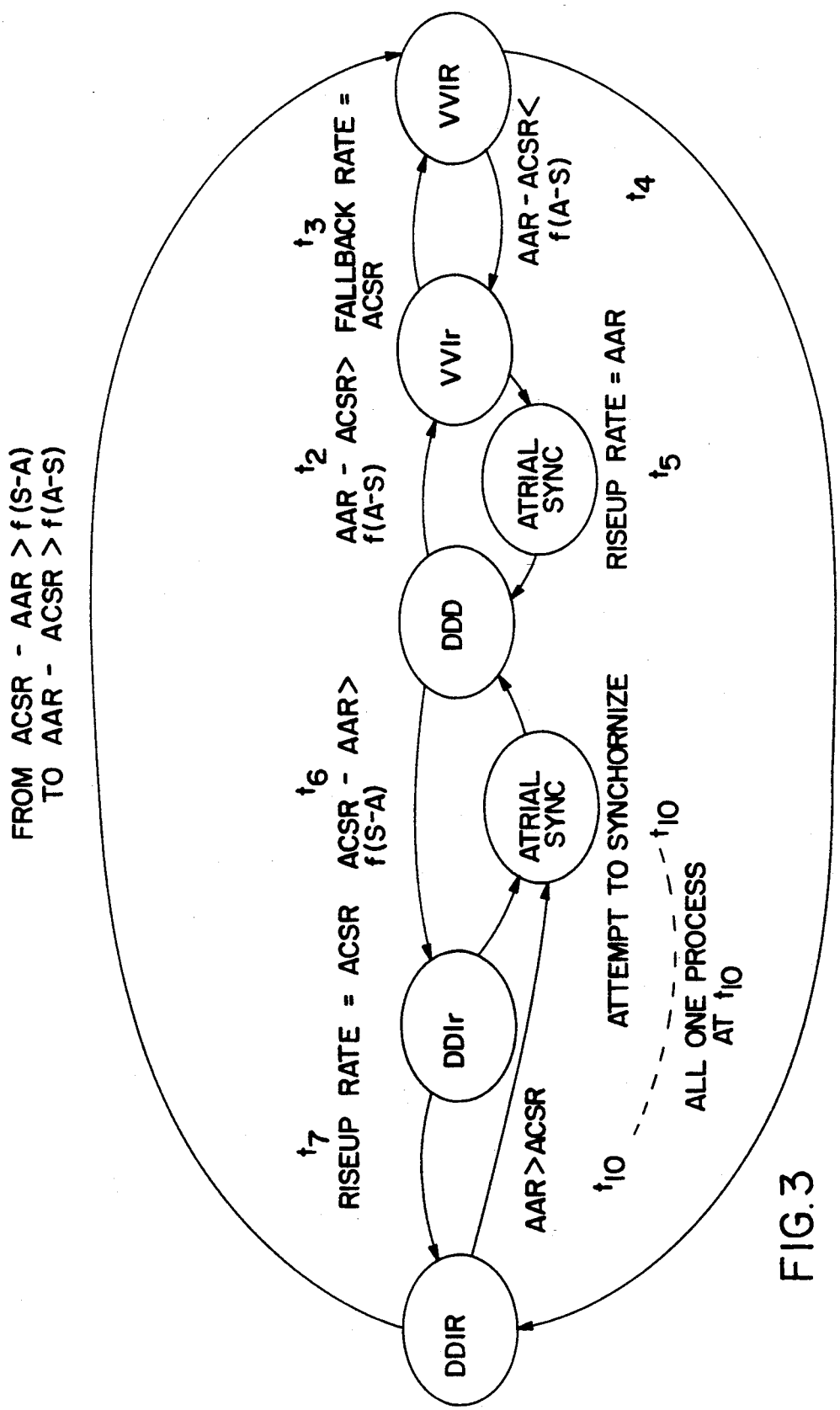
FIG. 3 is a state diagram of the operating states and transitions between operating states of the system of the present invention.

Turning now to FIGS. 2 and 3, the mode switching and tracking of the paced rate in beats per minute to the average atrial rate or the average combined sensor rate is depicted In FIG. 2, the AAR, the ACSR, and the paced rates are depicted in relation to one another and the AURL and SURL thresholds to show, over time, how the mode switches from DDD to VVIR, from VVIR to DDD, from DDD to DDIR, from DDIR to DDD and from DDD back to VVIR. Direct switching from VVIR to DDIR is possible if the AAR falls and the ACSR rises very rapidly, but such switching is not depicted in FIG. 2. In the state diagram of FIG. 3, the transitions from one mode to another are referenced to the events depicted chronologically in FIG. 2. These transitions with respect to both FIGS. 2 and 3 are explained as follows.

DDD to VVIR—In the DDD mode depicted in FIG. 2 from time o to $t_{1'}$, the AAR and ACSR are roughly equivalent, indicating that the patient s atrial rate is tracking his level of exercise Moreover, both the AAR and ACSR are well below the programmed AURL and SURL and above the LRL, indicating a stable heart condition and appropriate response to the level of exercise and emotional state of the patient At time $t_{1'}$, the AAR begins to increase above the ACSR at the onset of a bout of abnormal atrial tachycardia (extending part way through time $t_4$). When the AAR exceeds the ACSR by the A-S value (which is one of the programmed A-S set of values defining the A-S function to be explained hereafter) at time $t_2$, a mode transition takes place to the VVIr fallback mode which extends from time $t_2$ through time $t_3$. Automatic mode switching from DDD to the VVIr transition mode occurs on the next beat after the difference between the AAR and the ACSR exceeds the A-S function expressed in either beats per minute or in cycle lengths in milliseconds. In the VVIr fallback transition mode, the pacemaker operates in the VVI mode at smoothly declining rates while monitoring both the ACSR and AAR. Each V-V escape interval is decremented preferably at 20 milliseconds per interval during the VVIr transition mode. The VVIR mode is achieved when the VVIr rate becomes equal to or less than the ACSR.

This completes the mode switch from DDD to VVIR. As shown in FIG. 2, the atrial rate markedly exceeds the sensor derived ACSR as well as the AURL. These upper rate limits need not be exceeded to obtain the operation just described. If during VVIr fallback, the AAR and ASCR difference becomes less than the A-S function (not shown) then VVIr riseup would occur and the mode could switch back to DDD as shown hereafter at time $t_5$.

VVIR to DDD - At time $t_4$ in FIG. 2, the average atrial rate (AAR) has descended below the AURL and SURL and toward the ACSR until the difference falls below the then controlling A-S value of the programmable A-S function. At that point, the VVIr transition mode is again entered into wherein the VVIr pacing rate departs from the sensor derived rate and increases in a riseup mode toward the atrial rate. In that VVIr mode, the ACSR continues to be derived but is not employed to set the VVIr lower pacing rate but rather is employed only to continue the comparison between the AAR and ACSR. If during the VVIr mode, the AAR and ACSR rates diverge by more than the A-S function (not shown) then the mode would return to VVIR. When the incremented pacing rate reaches the AAR (shown at time $t_5$), the pacing mode switches to the DDD mode. The riseup in the VVIr pacing rate is also preferably at 20 milliseconds each V-V escape interval, and the switch to DDD with synchronization (Fig. 6) occurs at the first atrial sense that the time from the VS or VP to AS is greater than AURL interval minus the AV delay. This synchronization process may take several beats and may be forced if it does not occur in ten ventricular cycles.

As noted above, the AAR in the $t_2$-$t_4$ interval is depicted as exceeding both the AURL and the SURL whenever the ACSR is depicted as well below the SURL. The switching to the VVIR mode and back to the DDD mode could occur with an ACSR below the AURL and SURL that more closely tracks the AAR as long as the then controlling A-S values of the A S function were still exceeded (at $t_2$) and later returned to (at $t_4$) by the difference between the ACSR and AAR.

DDD to DDIR—During interval $t_5$ to $t_6$ the ACSR is compared to the AAR while the pacing rate is controlled by the instantaneous atrial rate in DDD mode. At time $t_6$, the ACSR exceeds the AAR by the then controlling S-A value of the programmed S A function, and thereafter the ACSR continues to rise. In this case, the DDIr with riseup transition mode is entered from $t_6$ to $t_7$. The riseup is accomplished by providing a V V interval shortening of 20 milliseconds per V V interval until it equals the V-V interval established by the ACSR at time $t_7$ when the mode switches to DDIR.

As shown in FIG. 2, the DDIR mode pacing rate tracks the ACSR so long as it is less than the SURL. However, when the ASCR exceeds the SURL from time $t_8$ to time $t_9$, the DDIR mode is rate limited at the SURL. From time $t_9$ to time $t_{10}$ the ACSR falls below the SURL, and the pacemaker tracks the ACSR in the DDIR mode.

DDIR to DDD In the interval from $t_6$ to $t_{10}$, the AAR is not computed, since AS events are expected to be suppressed by the synchronous atrial pacing at the rise up (DDIr) or the ASCR set (DDIR) escape intervals. Nevertheless, the underlying spontaneous atrial rate begins to generate AS events which reestablish a valid AAR at $t_{10}$. When AS events occur in the atrial synchronization window close to the time out of the APE signal, switching to the DDD mode can take place as explained further in conjunction with FIG. 6. At time $t_{10}$ the pacemaker makes an abrupt transition from the major DDIR mode to the major DDD mode at the point when the rising spontaneous atrial rate exceeds the falling sensor derived rate or ACSR, both being below the AURL and SURL respectively. The DDIR mode controls until synchronization as described hereafter in conjunction with FIG. 6 occurs. Thereafter the pacemaker operates in the DDD mode tracking the AAR from time $t_{10}$ to time $t_{11}$ whereupon the difference between the AAR and ACSR again exceeds the instantaneous A-S value of the programmable function and the transition from the DDD mode to the VVIr and VVIR modes is again commenced in a manner explained previously for times $t_2$ and $t_3$. It will be understood that if the ACSR had tracked the AAR within the A-S difference function, then the pacemaker would have continued to operate in the DDD mode at time $t_{11}$. It will also be understood that when the AAR or the instantaneous atrial rate exceeds the AURL, the pacing rate is governed by an atrial upper rate limit mode, such as the pseudo-Wenckebach mode, as shown in a portion of the interval from $t_{10}$ to $t_{11}$.

In FIG. 3 the major and transition modes and the mode switching conditions are depicted in a state diagram for convenience of explanation in conjunction with the timing diagram of FIG. 2. It will be appreciated that the mode switching states as described above may be implemented in a state machine of the type described in U.S. Pat. 4,944,298, incorporated herein by reference. In general, a mode state change is made dependent upon the current relationship of the AAR (or on AS in a synchronization timing window) with the ACSR and the prior mode or state. The relationship is governed by programmed A-S and S-A functions, together with the programmed AURL, SURL and LRL as illustrated in the rate domain in FIG. and in the interval domain in FIG. 5. As stated earlier, pacing systems conventionally employ fixed frequency clocks resulting in linear intervals and curvilinear rates. As a practical matter, the curvilinear S A and A-S functions depicted in FIG. 4 approximate linear functions within the ranges of interest when the terminal rate point (200 bpm, in FIG. 4) is set above the usable upper rate limits.

Figure 4:
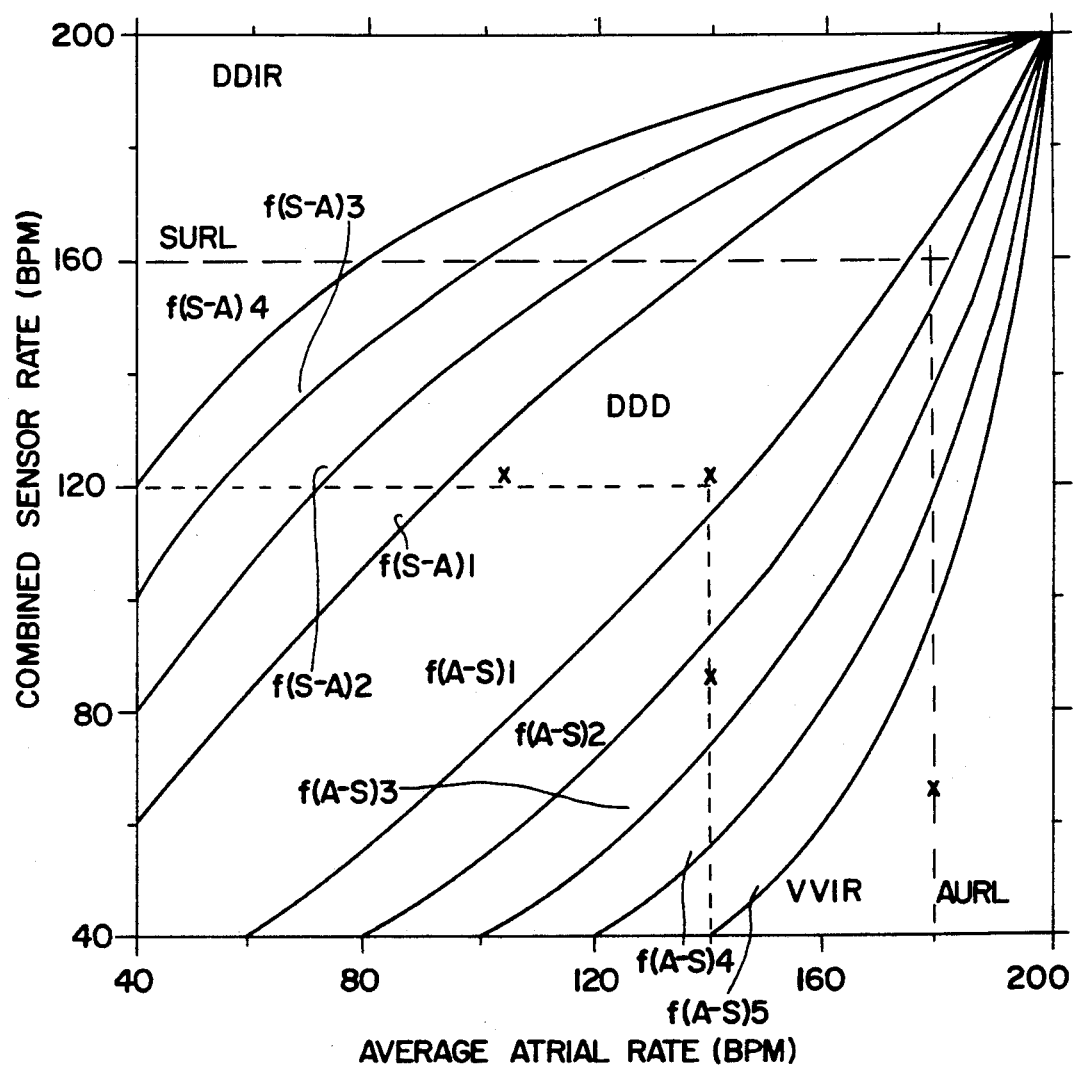
FIG. 4 is an illustration in the rate domain of the preferred mode switching functions between the VVIR, the DDD and the DDIR modes of operation for the relationship between the average atrial rate and the average combined sensor rate to a set of programmable functions.

Referring to FIG. 4, a LRL of 40 bpm is selected for both the ACSR and AAR and the SURL and AURL are depicted at 160 and 180 bpm, respectively. Four programmable f(S A) and five programmable f(A S) function curves are depicted which (when programmed in) mark the boundaries between the DDD, DDIR and VVIR major modes of operation. Thus, when one of f(S-A) and one of the f(A-S) functions are selected by programming the pacemaker of FIG. 1, the DDD mode controls when the ACSR and AAR values both fall in the control space between the two selected functions. In all other relationships of AAR to ACSR, the controlling mode is either the VVIR or DDIR mode. Thus, if $f(S-A)_1$ and $f(A-S)_2$ are programmed and the AAR=140 bpm while the ACSR=80 bpm, the VVIR mode will be entered into. However, if $f(A-S)_3$ were programmed, then the intersection of the 80 bpm and 140 bpm lines would fall between the selected S-A and A-S functions and the DDD mode would be entered into.

Figure 5:
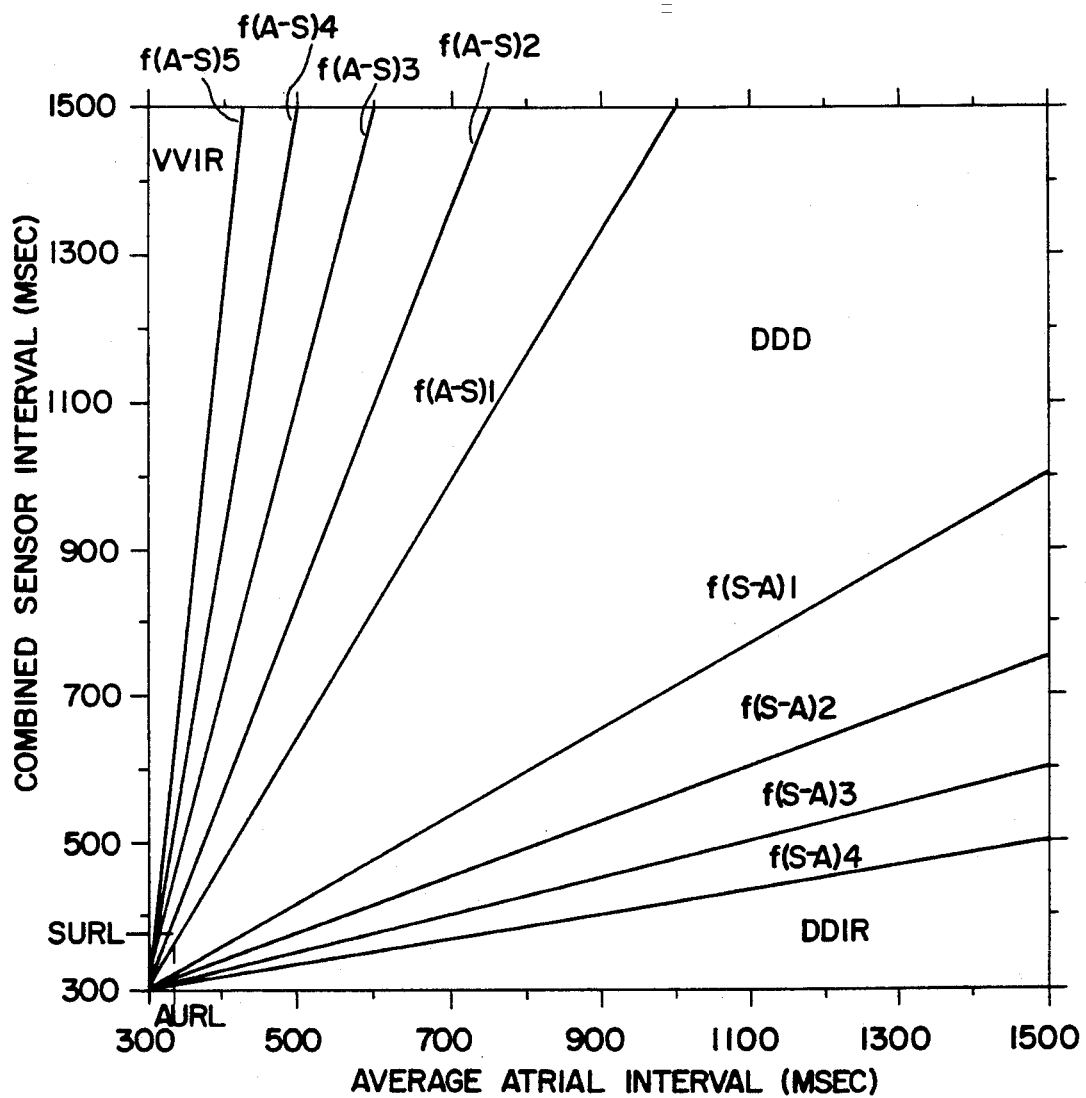
FIG. 5 is an illustration in the interval domain of the preferred mode switching functions between the VVIR, the DDD and the DDIR modes of operation for the relationship between the average atrial rate and the average combined sensor rate to a set of programmable functions.

Referring now to FIG. 5, the relationship of the S-A and A-S functions to average atrial and average combined sensor intervals between 300 ms (200 bpm) and 1500 ms (40 bpm) is illustrated simply to depict the relationships of FIG. 4 in the interval domain. Pacemaker pulse generators operating with a fixed clock frequency operate in the interval domain, resulting in the somewhat non-linear rate functions depicted in FIG. 4.

The manner in which the AAR and ACSR values are obtained shall now be explained. Detection of the atrial rate is critical to the mode switching rules in that determination of appropriateness of atrial rhythm is based in part on the atrial rate. Various means may be used to derive a rate value which can be used for this purpose. The mechanism for determining average atrial rate must allow reasonably quick reaction to abrupt changes in atrial rate but not allow undue action on the basis of a few premature atrial beats. Implementation considerations also include computation time and memory requirements. Irregular or erratic atrial sensing (oversensing or undersensing) can lead to erroneous rate information on which the pacemaker must make mode switching decisions.

The average atrial rate may be determined by a simple eight interval moving average or by a delta modulation process. When a delta modulation algorithm is employed, the AAR value (expressed as an interval) is initialized to the Lower Rate interval. With each AS and AP event, the preceding beat-to-beat interval is compared to the AAR. If the beat-to beat interval is less than the AAR interval, the AAR interval is reduced by the delta amount. If the beat to-beat interval is greater than the AAR interval, the AAR interval is increased by delta. If "x" successive beats require an increase or decrease, the delta itself may be increased. Delta is varied over the rate range so that the dither around a stable rate will be between 5 and 10 bpm in the physiologic rate range. The increase of delta during successive periods of increase or decrease allows the AAR to respond quickly to large and precipitous changes in rate. If the rate is stable, the AAR will dither around the actual rate at the beat-to-beat variation of delta. This technique mimics a low pass filter.

Not all atrial events can be used for the delta or average AAR calculations. There are situations where AS events do not occur such as during atrial pacing, so, where practical, atrial pacing is used. In DDIR pacing, AS events do not reset the timing of the pacemaker; thus, the interval from a previous AS or AP event until an AS event is used for the averaging calculation. However, the interval from an AS event to a subsequent AP is not used because it is indicative of neither the sensor derived nor spontaneous rates. To simplify implementation and explanation, the following rule is employed: all AS events are used for the determination of AAR except AS or AR followed by AP.

By the use of nearly all atrial events, input to the AAR delta tracking algorithm is maintained during atrial pacing and atrial sensing conditions, regardless of current mode. For situations where atrial events do not exist, such as during ventricular tachycardia or sensing of noise on the ventricular channel without atrial sensing, the AAR is not updated and is not used.

Loss of atrial capture may be reflected as tachycardia detection. In the event of loss of atrial capture, spontaneous atrial beats may follow. Counting both the paced and the spontaneous beats results in a high atrial rate which is likely to be determined to be tachycardia by the algorithm and cause a mode switch.

The following table illustrates the different atrial events which are used (USE) and ignored (NO) for determining the AAR.

| From this Event: | To this event: | | |
|---|---|---|---|
| | AP | AS | AR |
| AP | USE | USE | USE |
| AS | NO | USE | USE |
| AR | NO | USE | USE |

Turning now to the calculation of the ACSR, it may be derived from a single sensor by the methods employed in the Medtronic Activitrax ® and Legend TM activity responsive pacemakers and as described in Medtronic product literature. In such systems, the sensor is a piezoelectric activity sensor which develops a signal that is processed into a pacing rate control signal. It is also contemplated that in the present invention, the ACSR may be derived in the same fashion from one sensor (activity) or two or more physiologic sensors as taught, for example, in U.S. Patent Application Ser. No. 567,476 to Bennett, et al. filed Aug. 14, 1990. The signal processing algorithm(s) includes weighting factors that are programmable as described in the product literature and the '476 application. In any case, the ACSR value may be derived from the physiological sensor output(s) in accordance with any of the known techniques and employed with the AAR and the $f(S\ A)_n$ and $f(A-S)_n$ functions to effect mode switching as described hereinbefore.

Figure 6:
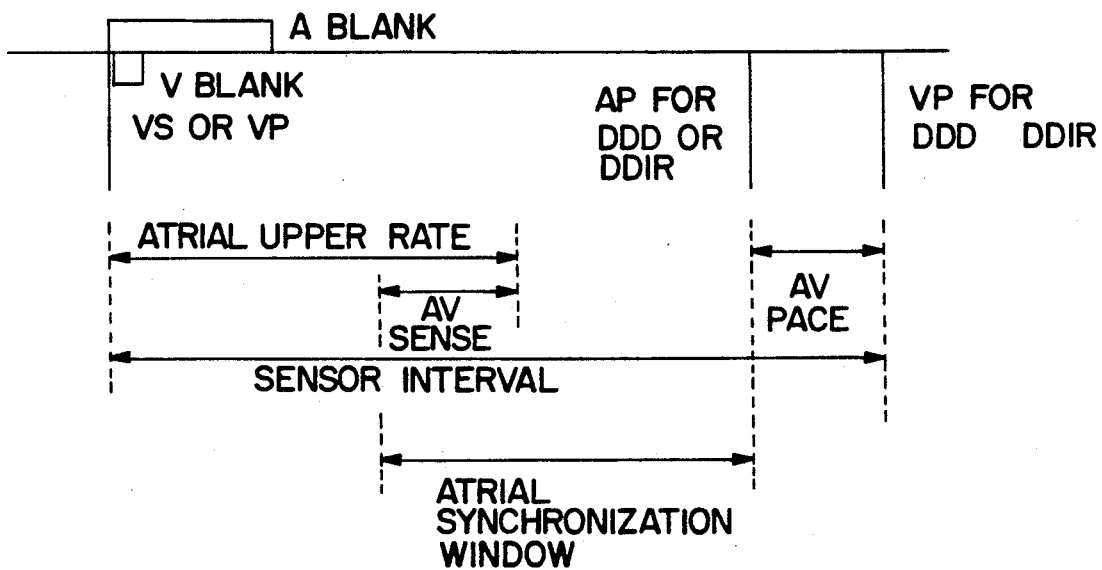
FIG. 6 shows beat-by-beat timing of the synchronization to DDD mode from other operating modes.

In the mode switch into DDD, it is desirable to make the switch at a point in the pacing escape interval outside the AURL interval less the AV interval. In accordance with the present invention, an atrial synchronization window (ASW) as depicted in FIG. 6 is preferably employed for synchronization. Thus, if an AS event occurs in one of ten successive ASWs depicted in FIG. 6, the mode is immediately switched to DDD on that AS event. If ten successive intervals pass with no AS event detected in the ASW, then the switch is forced at the scheduled AP event.

Although an exemplary embodiment of the present invention has been shown and described, it will be apparent to those having ordinary skill in the art that a number of changes, modifications, or alterations to the invention as described herein may be made, none of which depart from the spirit or scope of the present invention. All such changes, modifications, and alterations should therefore be seen as within the scope of the present invention. Accordingly, the complete scope of the present invention should be determined with reference to the claims set forth below.

What is claimed is:

1. A method of operating a programmable dual chamber, rate-responsive pacemaker capable of operating in more than one pacing mode and provided with atrial and ventricular sensing input and stimulation output circuitry and control logic means for operating said pacemaker in an atrial synchronous mode providing ventricular stimulation output pulses synchronously with sensed atrial depolarizations, and in at least one further rate responsive pacing mode providing atrial and/or ventricular stimulation output pulses on demand at a rate dependent upon a sensor related pacing rate control signal, comprising the steps of:

monitoring atrial heart beats;

developing an average atrial heart rate/interval from successive atrial heart beats;

providing at least one physiologic sensor for sensing a patient's physiologic requirements of cardiac output and providing a sensor output signal in response thereto;

developing a sensor related pacing rate/interval from said sensor output signal;

establishing a sensor driven upper pacing rate limit for pacing said further pacing mode;

establishing an atrial synchronous upper pacing rate limit for pacing in said atrial synchronous pacing mode;

establishing a lower pacing rate limit;

establishing a first mode switching boundary function defining a first set of correlated sensor related and average atrial pacing rate/interval values, wherein the sensor related rate/interval values set a pacing rate greater than the average atrial rate, through the range of possible rate/interval values between said lower pacing rate limit and said atrial synchronous upper pacing rate limit;

establishing a second mode switching boundary function defining a second set of correlated sensor related and average atrial pacing rate/interval values, wherein the average atrial rate/interval values set a pacing rate greater than the sensor related rate, through the range of possible rate/interval values between said lower pacing rate limit and said sensor driven upper pacing rate limit;

periodically comparing the average atrial and sensor related rate/interval values to the first and second mode switching boundary function values; and operating said pacemaker in said atrial synchronous mode as long as the correlated sensor related and average atrial rate/interval values do not match a value falling outside the first and second mode switching functions.

2. The method of claim 1 wherein said rate responsive pacing mode comprises first and second rate responsive pacing modes and further comprising the steps of:

operating said pacemaker in said first rate responsive pacing mode when said correlated sensor related and average atrial rate/interval values match a point falling outside the first mode switching boundary function; and operating said pacemaker in said second rate responsive pacing mode when said correlated sensor related and average atrial rate/interval values match a point falling outside the second mode switching boundary function.

3. The method of claims 1 or 2 wherein said atrial synchronous pacing mode is the DDD pacing mode.

4. The method of claim 2 wherein said first and second rate responsive pacing modes are the DDIR and VVIR pacing modes, respectively.

5. The method of claims 1 or 2 wherein said atrial synchronous pacing mode is the DDD pacing mode and wherein said first and second rate responsive pacing modes are the DDIR and VVIR pacing modes, respectively.

6. The method of claims 1 or 2 further comprising the steps of:

remotely programming the first and second mode switching boundary function values; and remotely programming the atrial synchronous and sensor driven upper pacing rate limit and the lower pacing rate limit values.

7. The method of claim 2 further comprising the steps of:

switching pacing modes between said atrial synchronous and said first and second rate responsive pacing modes when the correlated sensor related and average atrial rate/interval values change from a point falling within or outside one or both of said first and second mode switching boundary functions; and operating said pacemaker in pacing rate transition modes for avoiding abrupt pacing rate changes between sensor related and average atrial rates upon switching pacing modes until the pacing rate matches the switched to sensor related or average atrial rate.

8. The method of claim 7 wherein said atrial synchronous pacing mode is the DDD pacing mode.

9. The method of claim 7 wherein said first and second rate responsive pacing modes are the DDIR and VVIR modes, respectively.

10. The method of claim 7 wherein said atrial synchronous pacing mode is the DDD pacing mode and wherein said first and second rate responsive pacing modes are the DDIR and VVIR pacing modes, respectively.

11. The method of claim 7 further comprising the steps of:

remotely programming the first and second mode switching boundary function values; and remotely programming the atrial synchronous and sensor driven upper pacing rate limit and the lower pacing rate limit values.

12. Apparatus for operating a programmable dual chamber, rate responsive pacemaker capable of operating in more than one pacing mode and provided with atrial and ventricular input and stimulation output circuitry and control logic means for operating said pacemaker in an atrial synchronous mode providing ventricular stimulation output pulses synchronously with sensed atrial depolarizations, and in at least one further rate responsive pacing mode providing atrial and/or ventricular stimulation output pulses on demand at a rate dependent upon a sensor related pacing rate control signal, comprising the steps of:

means for monitoring atrial heart beats;

means for developing an average atrial heart rate/interval from successive atrial heart beats;

means for providing at least one physiologic sensor for sensing a patient's physiologic requirements of cardiac output and providing a sensor output signal in response thereto;

means for developing a sensor related pacing rate/interval from said sensor output signal;

means for establishing a sensor driven upper pacing rate limit for pacing said further pacing mode;

means for establishing an atrial synchronous upper pacing rate limit for pacing in said atrial synchronous pacing mode;

means for establishing a lower pacing rate limit;

means for establishing a first mode switching boundary function defining a first set of correlated sensor related and average atrial pacing rate/interval values, wherein the sensor related rate/interval valves set a pacing rate greater than the average atrial rate, through the range of possible rate/interval values between said lower pacing rate limit and said atrial synchronous upper pacing rate limit;

means for establishing a second mode switching boundary function defining a second set of correlated sensor related and average atrial pacing rate/interval values, wherein the average atrial rate/interval values set a pacing rate greater than the sensor related rate, through the range of possible rate/interval values between said lower pacing rate limit and said sensor driven upper pacing rate limit;

means for periodically comparing the average atrial and sensor related rate/interval values to the first and second mode switching boundary function values; and means for operating said pacemaker in said atrial synchronous mode as long as the correlated sensor related and average atrial rate/interval values do not match a value falling outside the first and second mode switching boundary functions.

13. The apparatus of claim 12 wherein said rate responsive pacing mode comprises first and second rate responsive pacing modes and further comprising:

means for operating said pacemaker in said first rate responsive pacing mode when said correlated sensor related and average atrial rate/interval values match a point falling outside the first mode switching boundary function; and means for operating said pacemaker in said second rate responsive pacing mode when said correlated sensor related and average atrial rate/interval values match a point falling outside the second mode switching boundary function.

14. The apparatus of claim 12 wherein said atrial synchronous pacing mode is the DDD pacing mode.

15. The apparatus of claim 12 wherein said first and second rate responsive pacing modes are the DDIR and VVIR pacing modes, respectively.

16. The apparatus of claim 12 wherein said atrial synchronous pacing mode is the DDD pacing mode and wherein said first and second rate responsive pacing modes are the DDIR and VVIR pacing modes, respectively.

17. The apparatus of claim 12 further comprising:

means for remotely programming the first and second mode switching boundary function values; and means for remotely programming the atrial synchronous and sensor driven upper pacing rate limit and the lower pacing rate limit values.

18. The apparatus of claim 12 further comprising:

means for switching pacing modes between said atrial synchronous and said first and second rate responsive pacing modes when the correlated sensor related and average atrial rate/interval values change from a point falling within or outside one or both of said first and second mode switching boundary functions; and means for operating said pacemaker in pacing rate transition modes for avoiding abrupt pacing rate changes between sensor related and average atrial rates upon switching pacing modes until the pacing rate matches the switched to sensor related or average atrial rate.

19. The apparatus of claim 18 wherein said atrial synchronous pacing mode is the DDD pacing mode.

20. The apparatus of claim 18 wherein said first and second rate responsive pacing modes are the DDIR and VVIR modes, respectively.

21. The apparatus of claim 18 wherein said atrial synchronous pacing mode is the DDD pacing mode and wherein said first and second rate responsive pacing modes are the DDIR and VVIR pacing modes, respectively.

22. The apparatus of claim 18 further comprising:

means for programming the first and second mode switching boundary function values; and means of remotely programming the atrial synchronous and sensor driven upper pacing rate limit and the lower pacing rate limit values.

* * * * *

UNITED STATES PATENT AND TRADEMARK OFFICE
CERTIFICATE OF CORRECTION

PATENT NO. : 5,144,949

DATED : September 8, 1992

INVENTOR(S) : Walter H. Olson

It is certified that error appears in the above-indentified patent and that said Letters Patent is hereby corrected as shown below:

Column 2, Line 1, delete "A. Berstein al,", and insert in its place --A. Berstein et al.,--.

Column 9, Line 40, delete "A S", and insert in its place --A-S--.

Column 9, Line 47, delete "S A", and insert in its place --S-A--.

Column 9, Line 50, delete "VV", and insert in its place --V-V--.

Column 9, Line 51, delete "VV", and insert in its place --V-V--.

Column 10, Line 38, delete "FIG.", and insert in its place --Figure 4--.

Column 10, Line 42, delete "S A", and insert in its place --S-A--.

Column 10, Line 49, delete "f(S A)", and insert in its place --f(S-A)--.

Column 10, Line 49, delete "f(A S)", and insert in its place --f(A-S)--.

Column 12, Line 29, delete "f(S A)$_n$", and insert in its place --f(S-A)$_n$--.

Column 14, Line 36, before "input", please insert --sensing--.

UNITED STATES PATENT AND TRADEMARK OFFICE
CERTIFICATE OF CORRECTION

PATENT NO. : 5,144,949
DATED : September 8, 1992
INVENTOR(S) : Walter H. Olson

It is certified that error appears in the above-indentified patent and that said Letters Patent is hereby corrected as shown below:

Column 16, Line 34, before "programming", please insert —remotely—.

Signed and Sealed this

Eighth Day of November, 1994

Attest:

BRUCE LEHMAN

Attesting Officer

Commissioner of Patents and Trademarks